(12) United States Patent
Feng et al.

(10) Patent No.: US 10,260,949 B2
(45) Date of Patent: Apr. 16, 2019

(54) RAMAN SPECTRUM-BASED OBJECT INSPECTION APPARATUS AND METHOD

(71) Applicant: Nuctech Company Limited, Beijing (CN)

(72) Inventors: Huacheng Feng, Beijing (CN); Yumin Yi, Beijing (CN); Hongqiu Wang, Beijing (CN); Rui Fan, Beijing (CN); Shixin Zhang, Beijing (CN)

(73) Assignee: Nuctech Company Limited, Beijing (CN)

( * ) Notice: Subject to any disclaimer, the term of this patent is extended or adjusted under 35 U.S.C. 154(b) by 0 days.

(21) Appl. No.: 15/827,209

(22) Filed: Nov. 30, 2017

(65) Prior Publication Data

US 2018/0180482 A1 Jun. 28, 2018

(30) Foreign Application Priority Data

Dec. 26, 2016 (CN) .......................... 2016 1 1219313

(51) Int. Cl.
*G01J 3/44* (2006.01)
*G01J 5/00* (2006.01)
*G01N 21/65* (2006.01)
*G08B 21/02* (2006.01)
(Continued)

(52) U.S. Cl.
CPC ............. *G01J 3/4412* (2013.01); *G01J 3/44* (2013.01); *G01J 5/0003* (2013.01); *G01N 21/65* (2013.01); *G01N 21/95* (2013.01); *G06T 7/0002* (2013.01); *G08B 21/02* (2013.01)

(58) Field of Classification Search
CPC ........ G01J 3/02; G01J 3/44; G01J 3/18; G01J 5/00; G01N 21/65; G06T 7/00
See application file for complete search history.

(56) References Cited

U.S. PATENT DOCUMENTS

2007/0076942 A1* 4/2007 Yatsugake .......... G01N 21/9501
382/141
2012/0062874 A1 3/2012 Beckstead et al.
(Continued)

FOREIGN PATENT DOCUMENTS

EP 2 889 608 A2 7/2015

OTHER PUBLICATIONS

Extended European Search Report for European Patent Application No. 17204811.8 dated Feb. 22, 2018.

*Primary Examiner* — Abdullahi Nur
(74) *Attorney, Agent, or Firm* — Knobbe, Martens, Olson & Bear LLP

(57) ABSTRACT

A Raman spectrum-based object inspection apparatus and a Raman spectrum-based object inspection method are disclosed. In one aspect, an example apparatus includes: a laser device configured to emit a laser; an optical guiding device configured to guide the laser to an object to be detected and collect a Raman scattering light from the object. The apparatus includes a spectrum generator configured to receive the Raman scattering light collected by the optical guiding device and generate a Raman spectroscopic signal. The spectrum analyzer is configured to analyze the Raman spectroscopic signal to obtain an inspection result. The apparatus includes a monitoring device configured to monitor a state of the object and control an object inspection operation depending on the state of the object.

14 Claims, 7 Drawing Sheets

(51) Int. Cl.
*G01N 21/95* (2006.01)
*G06T 7/00* (2017.01)

(56) References Cited

U.S. PATENT DOCUMENTS

| | | | |
|---|---|---|---|
| 2012/0224168 A1* | 9/2012 | Hirai | H04B 10/071 |
| | | | 356/73.1 |
| 2015/0168367 A1* | 6/2015 | Gardner | G01N 33/227 |
| | | | 356/72 |
| 2015/0192462 A1 | 7/2015 | Schiering et al. | |
| 2015/0294076 A1* | 10/2015 | Treado | G01N 21/65 |
| | | | 506/12 |

* cited by examiner

RAMAN SPECTRUM-BASED OBJECT INSPECTION APPARATUS AND METHOD

CROSS-REFERENCE TO RELATED APPLICATION

This application claims priority to Chinese Patent Application No. 201611219313.1 filed on Dec. 26, 2016, the disclosure of which is hereby incorporated by reference in its entirety for all purposes.

BACKGROUND OF THE DISCLOSED TECHNOLOGY

Field of the Technology

The disclosed technology generally relates to Raman spectrum detection technology, and in particular to a Raman spectrum-based object inspection apparatus and a Raman spectrum-based object inspection method.

Description of the Related Technology

In recent years, Raman spectrum analysis technology has been widely applied in fields such as inspection of hazardous articles and recognition of substance. In the field of inspection of hazardous articles, since the forms of violent attacks of terrorists in public spaces become more and more diversified, various hazardous chemicals have become one of main tools of committing a crime for the terrorists. In consideration of such circumstance, the security inspection organizations have added new requirements on inspection of the hazardous chemicals besides the conventional inspection of luggage packing security inspection. In addition, in the field of recognition of substances, the people often cannot judge properties of the substances correctly as various substances have different colors and shapes. The Raman spectrum depends on level structure of molecules of the object to be detected, thus, the Raman spectrum may be used as "fingerprint" information of substances for recognizing substances. Therefore, the Raman spectrum analysis technology has been applied broadly in fields of such as customs, common security, foods, drugs, environments.

In applications of the Raman spectrum analysis technology, various substances may have different physical properties due to difference of the objects to be detected. These objects may have different thermal sensitivities to laser irradiation in the Raman spectrum analysis technology. The conventional Raman spectrum inspection instruments have no functions of monitoring process of the Raman spectrum inspection.

SUMMARY OF THE DISCLOSURE

An embodiment of the disclosed technology provides a Raman spectrum-based object inspection apparatus, including: a laser device configured to emit a laser; an optical guiding device configured to guide the laser to an object to be detected and collect a Raman scattering light from the object; a spectrum generator configured to receive the Raman scattering light collected by the optical guiding device and generate a Raman spectroscopic signal; a spectrum analyzer configured to analyze the Raman spectroscopic signal to obtain an inspection result; and a monitoring device configured to monitor a state of the object and control an object inspection operation depending on the state of the object.

An embodiment of the disclosed technology also provides a Raman spectrum-based object inspection method, including: monitoring a state of an object to be detected to determine whether the state of the object is normal or abnormal; when the state of the object is normal, starting a laser device to emit a laser to the object and collecting a Raman scattering light from the object to detect a Raman spectrum of the object; otherwise, when the state of the object is abnormal, terminating the laser device to stop emitting the laser to interrupt detection.

DETAILED DESCRIPTION OF CERTAIN ILLUSTRATIVE EMBODIMENTS

Figure 1:
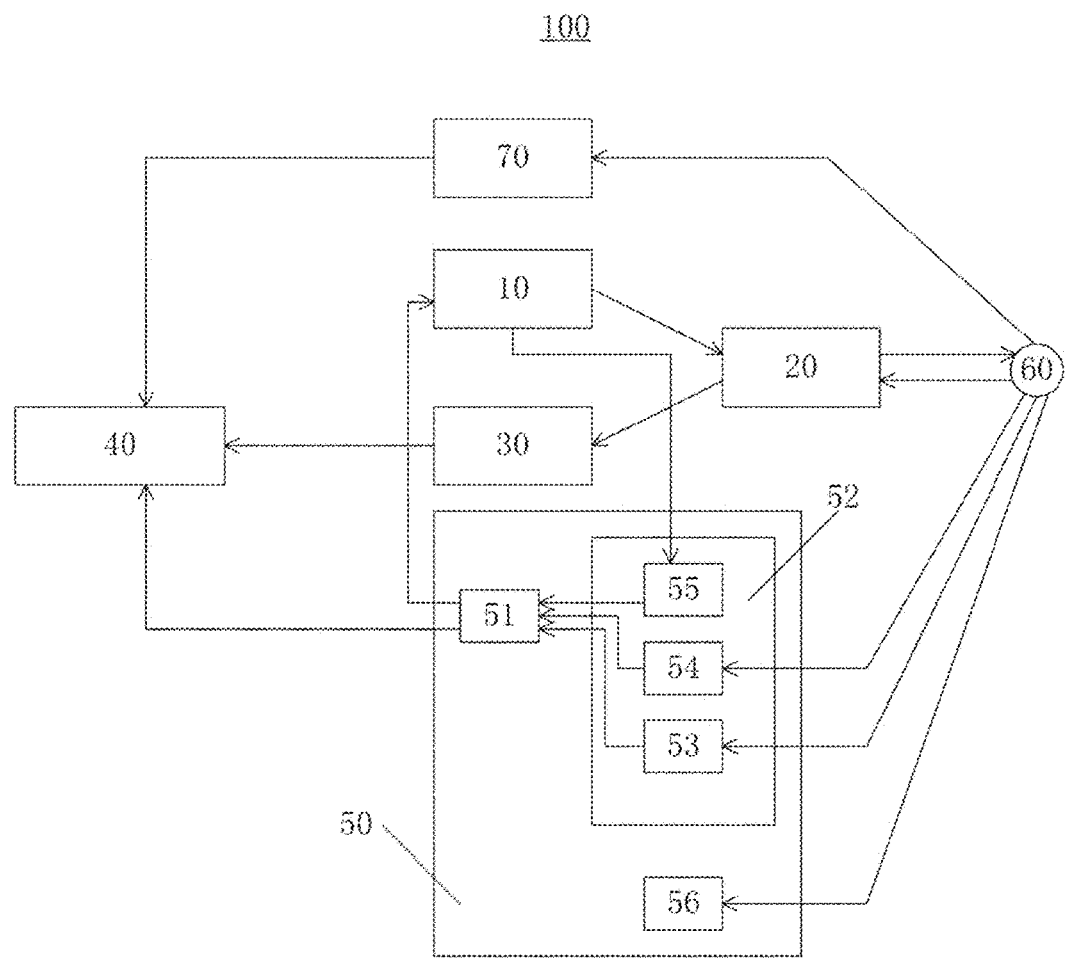
FIG. 1 is a schematic view showing a structure of a Raman spectrum-based object inspection apparatus according to an embodiment of the disclosed technology.

Technical solutions of the disclosed technology will be described hereinafter in more detail by the way of embodiments with reference to the attached drawings. The same or similar reference numerals refer to the same or similar elements throughout the description. The explanation to the embodiments of the disclosed technology with reference to the attached drawings is intended to interpret the general concept of the disclosed technology, rather than being construed as a limiting to the disclosed technology.

FIG. 1 is a schematic view showing a Raman spectrum-based object inspection apparatus 100 according to an embodiment of the disclosed technology. The object inspection apparatus 100 includes: a laser device 10 configured to emit a laser; an optical guiding device 20 configured to guide the laser to an object 60 to be detected and collect a Raman scattering light from the object 60; a spectrum generator 30 configured to receive the Raman scattering light collected by the optical guiding device 20 and generate a Raman spectroscopic signal; a spectrum analyzer 40 configured to analyze the Raman spectroscopic signal to obtain an inspection result; and a monitoring device 50 configured to monitor a state of the object 60 and control an object inspection operation depending on the state of the object 60.

The Raman spectrum analysis technology is applied widely, thus it may be used to detect various objects which may have different physical properties and have different thermal sensitivities to laser irradiation of the Raman spectrum analysis technology. Certain substances may become hazardous when they are irradiated by the laser, for example, they may be ignited, burned, even exploded. Before inspection, it often cannot determine the properties of the object to be detected clearly. Thus, for the sake of security, the object inspection apparatus 100 in the embodiment of the disclosed technology is provided with the monitoring device 50. The monitoring device 50 may be configured to monitor the state of the object 60. When the monitoring device 50 finds an abnormal state of the object 60, it may terminate the operation of the object inspection apparatus 100 timely to avoid dangers or incorrect detection results.

In an example, the monitoring device 50 may include: a control unit 51 and an information acquiring unit 52. The information acquiring unit 52 is configured to acquire information on the state of the object 60. The control unit 51 is configured to start or terminate the object inspection operation depending on the information on the state of the object 60. As an example, the information on the state of the object 60 may include color information of a detected location of the object. Correspondingly, the information acquiring unit 52 may include a photographic unit 53. The photographic unit 53 may be configured to shot (e.g., shoot, for example capture) the detected location of the object 60 to acquire information on color of the detected location. As an example, when the detected location becomes black, it typically means that the detected location has been burned. Thus, when the photographic unit 53 captures black color of the detected location, the control unit 51 may be configured to terminate the object inspection operation, for example, to stop the laser device to emit the laser or the like. As an example, the photographic unit 53 may include any known photographic tools such as a camera or webcam. The photographic unit 53 may capture an image of the entire object or a part of the object and capture information on state of the object, such as colors, shapes. It should be understood that black color is only an example as discussed in the above paragraphs, however, the embodiments of the disclosed technology are not limited to this, for example, the control unit 51 may also be configured to terminate the object inspection operation when the photographic unit 53 has captured other predetermined colors or a combination of multiple colors of the detected location.

In an example, the information acquiring unit 52 includes a temperature measuring unit 54 configured to measure a temperature of the object 60 in the object inspection operation. By means of the temperature measuring unit 54, the temperature of the object 60 under laser irradiation may be measured such that it can be monitored whether an increasing speed (slope of variation) of the temperature or amplitude of the temperature of the object exceeds a predetermined threshold, or not. The threshold may be determined depending on work temperature that the specific materials of the object to be detected and the optical guiding device permit, for example, the threshold of the amplitude of the temperature may be 80 Celsius degrees or 100 Celsius degrees; the threshold of the slope of variation of the temperature may be 10 Celsius degrees per second or the like. As an example, when the amplitude of the temperature or the slope of variation of the temperature of the object exceeds the predetermined threshold, it often means that there is danger of the object being ignited, burned or exploded. Thus, as an example, the control unit 51 may be configured to terminate the object inspection operation, for example, to stop the laser device to emit the laser, when the slope of variation of the temperature or the amplitude of the temperature of the object exceeds the predetermined threshold. As an example, the temperature measuring unit 54 may include one or more infrared temperature measuring device, or may include other known temperature measuring devices in the art. As an example, the temperature measuring device 54 may measure the temperature in non-contact manner or in contact manner.

In an example, the information acquiring unit 52 may further include a laser irradiation danger recognizing unit 55. The laser irradiation danger recognizing unit 55 may be configured to recognize whether a non-irradiated target (an unfavorably-irradiated target) falls within a region which is being irradiated by the laser or will be irradiated by the laser. For example, the laser irradiation danger recognizing unit 55 may be a photographic device which can recognize the non-irradiated target. As an example, the non-irradiated target includes a face of a person, even eyes of the person. In an example, the laser irradiation danger recognizing unit 55 may be configured to monitor whether the face or eyes of the person falls within the region that may be irradiated by the laser or not. Once it finds that the face or eyes of the person falls within the region that may be irradiated by the laser, the control unit 51 will terminate the object inspection operation immediately, for example, stop the laser device to emit the laser, so as to avoid danger.

In the above embodiments, the information acquiring unit 52 may include any one of the photographic unit 53, the temperature measuring unit 54 and the laser irradiation danger recognizing unit 55, or may include any combination thereof. As an example, the information acquiring unit 52 may include one or more photographic devices. As an example, the photographic unit 53 and the laser irradiation danger recognizing unit 55 may also be implemented by the same photographic device. Any one or two of the photographic unit 53, the temperature measuring unit 54 and the laser irradiation danger recognizing unit 55 may be integrated with the spectrum analyzer 40. As an example, in the object inspection apparatus 100 according to the embodiment of the disclosed technology, one or more laser devices 10, one or more spectrum generators 30 (such as spectrometers), one or more optical guiding devices 20 may be provided.

In an example, the monitoring device 50 may further include a recording unit 56 configured to record a physical image of the object 60. By means of the recording unit 56, the substance information detected by the Raman spectrum analysis technology and physical image such as appearance shapes of the object may be recorded simultaneously, such as for obtaining evidence, information recording and transporting in practice.

As an example, the optical guiding device 20 may include a combination of separated optical elements or may be formed by optical fiber probes. The spectrum generator 30 may for example be implemented by a spectrometer. The spectrum analyzer 40 may for example be implemented by a data processing device (such as a computer, a microprocessor, or the like), or may be implemented by the spectrometer which has a data processing function. In an example, the spectrum analyzer 40 may include a storing unit configured to store a reference Raman spectrum library, a comparing unit configured to compare the detected Raman spectroscopic signal with reference Raman spectroscopic signals in the reference Raman spectrum library to determine the composition of the object and an outputting unit configured to output results of the comparison of the comparing unit. As an example, barcodes corresponding to the respective reference Raman spectroscopic signals in the reference Raman spectrum library may also be stored in the storing unit in the spectrum analyzer 40; the comparing unit may determine information of barcode corresponding to the reference Raman spectroscopic signal matched with the detected Raman spectroscopic signal; and the outputting unit may also be configured to output the barcode as one of the results.

Figure 2:
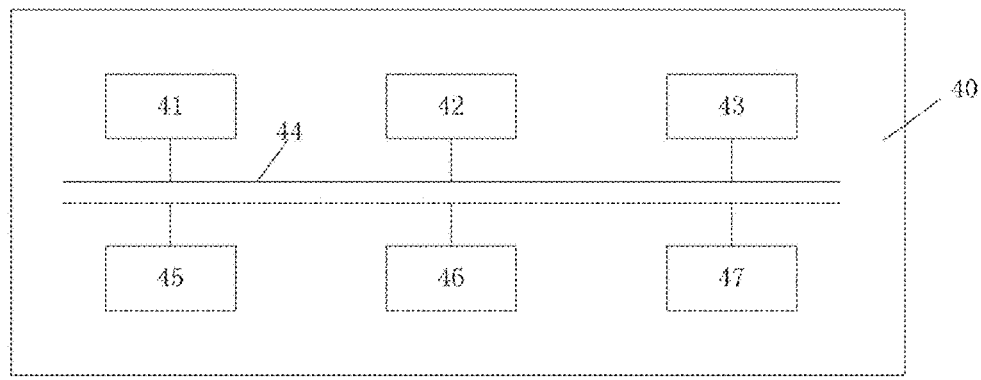
FIG. 2 is a schematic view showing modules of a spectrum analyzer in the Raman spectrum-based object inspection apparatus according to an embodiment of the disclosed technology.

As an example, in view of physical structure, as shown in FIG. 2, the spectrum analyzer 40 may include: a data acquisition memory 41, a read-only memory (ROM) 42, a random access memory (RAM) 43, an internal bus 44, an input device 45, a processor 46 and a display device 47. The data acquisition memory 41 is configured to store the Raman spectroscopic signal data collected from the spectrum generator 30 (for example the spectrometer). The read-only memory 42 is configured to store configuration information of the spectrum analyzer 40 (such as data processing device) and programs. The random access memory 43 is configured to store various data temporarily during the operation of the processor 46. By means of the input device 45 (such as buttons, a sensor, a keyboard, a mouse, or the like), a user may input operation instructions. The processor 46 is configured to carry out data processing operation. The display device 47 is configured to output calculation results. In addition, computer programs for data processing may also be stored in the data acquisition memory 41. The internal bus 44 connects the data acquisition memory 41, the read-only memory 42, the random access memory 43, the input device 45, the processor 46 and the display device 47.

After the user inputs operation commands by the input device 45, instruction codes in the computer programs request the processor to carry out a predetermined data processing algorithm. After the data processing results are obtained, the data processing results may be displayed on the display device 47 such as a LCD display, or be outputted directly by a hard copy.

Figure 3:
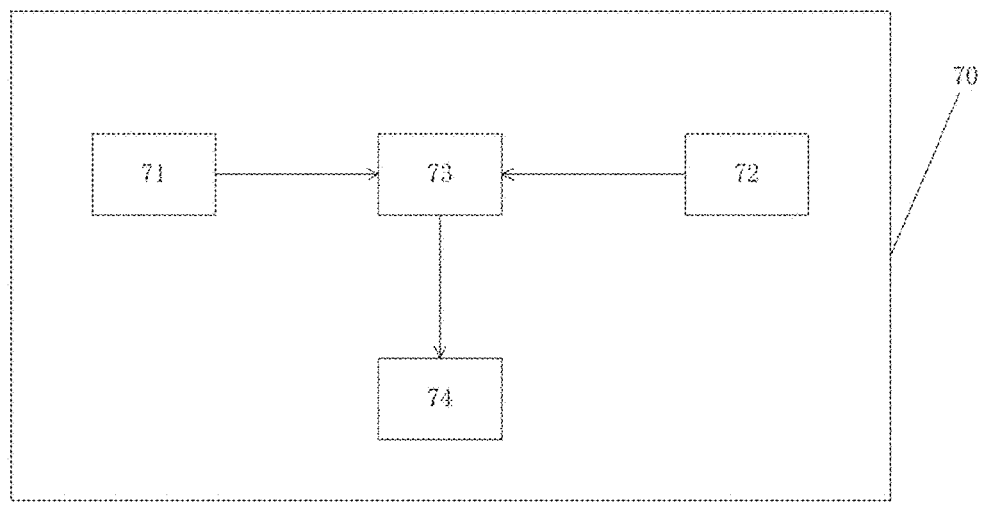
FIG. 3 is a schematic view showing modules of a weight recognizing device in the Raman spectrum-based object inspection apparatus according to an embodiment of the disclosed technology.
Figure 4:
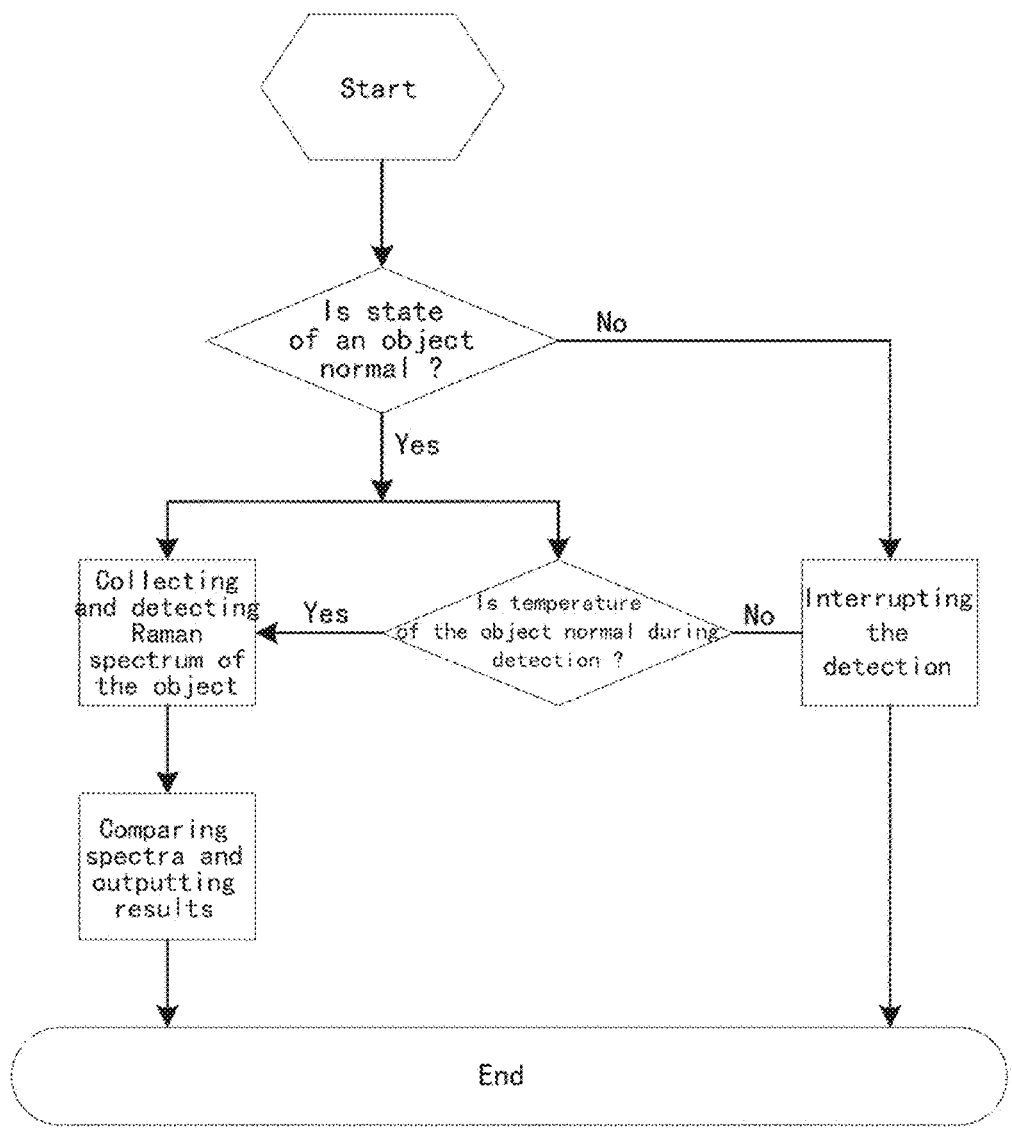
FIG. 4 is a flow chart of a Raman spectrum-based object inspection method according to an embodiment of the disclosed technology.

In an embodiment, the Raman spectrum-based object inspection apparatus 100 may further include a weight recognizing device 70 configured to identify the object depending on weight of the object 60 to be detected. As an example, as illustrated in FIG. 3, the weight recognizing device 70 may include: a weighing unit 71 configured to measure the weight of the object 60; a storing unit 72 configured to store predetermined reference weights and database of the corresponding barcodes; a comparing unit 73 configured to compare the measured weight of the object 60 with the reference weight to determine the barcode corresponding to the reference weight which is closest to the weight of the object; and an outputting unit 74 configured to output the determined barcode as a weight recognizing result.

By means of the weight recognizing device 70, an operator may determine composition of the object by combining the Raman spectrum analysis and weight analysis, so as to improve reliability and accuracy of the object inspection results.

As an example, the weight recognizing device 70 and the spectrum analyzer 40 may be implemented by the same data processing device (such as a computer, a microprocessor, or the like), or may be implemented by different data processing devices respectively.

As an example, the control unit 51 in the monitoring device 50 and the weight recognizing device 70 or the spectrum analyzer 40 may also be implemented by the same data processing device (such as a computer, a microprocessor, an embedded system, or the like), or the control unit may be implemented by a data processing device separated from the weight recognizing device 70 and the spectrum analyzer 40.

An embodiment of the disclosed technology also provides a Raman spectrum-based object inspection method, including:

monitoring a state of an object to be detected to determine whether the state of the object is normal or abnormal;

when the state of the object is normal, starting a laser device to emit a laser to the object and collecting a Raman scattering light from the object to detect a Raman spectrum of the object; otherwise, when the state of the object is abnormal, terminating the laser device to stop emitting the laser to interrupt detection.

In an example, the state of the object includes a color of the object. The abnormal state of the object includes a predetermined color of the object (for example, black or another color, or a combination of multiple colors) while the normal state of the object includes any colors of the object other than the predetermined color (for example, a color other than black).

In an example, the Raman spectrum-based object inspection method may further include: when the state of the object is normal, starting a real-time monitoring of the temperature of the object during detection, and when the temperature of the object is found to exceed a predetermined threshold, terminating the laser device to stop emitting the laser to interrupt the detection.

In an example, the Raman spectrum-based object inspection method may further include: comparing the detected Raman spectrum with reference Raman spectra and outputting results of the comparing.

As an example, the Raman spectrum-based object inspection method may further include: imaging entirety or part of the object to form a physical image and recording the physical image. It may record substance information detected by the Raman spectrum analysis technology and the physical image such as appearance shapes of the object simultaneously, such as for obtaining evidence, information recording and transporting in practice.

The Raman spectrum-based object inspection apparatus and method according to the embodiments of the disclosed technology can perform substance recognition and monitor operation process efficiently to improve security of inspection, in particular, suitable for inspection of hazardous objects.

Figure 5:
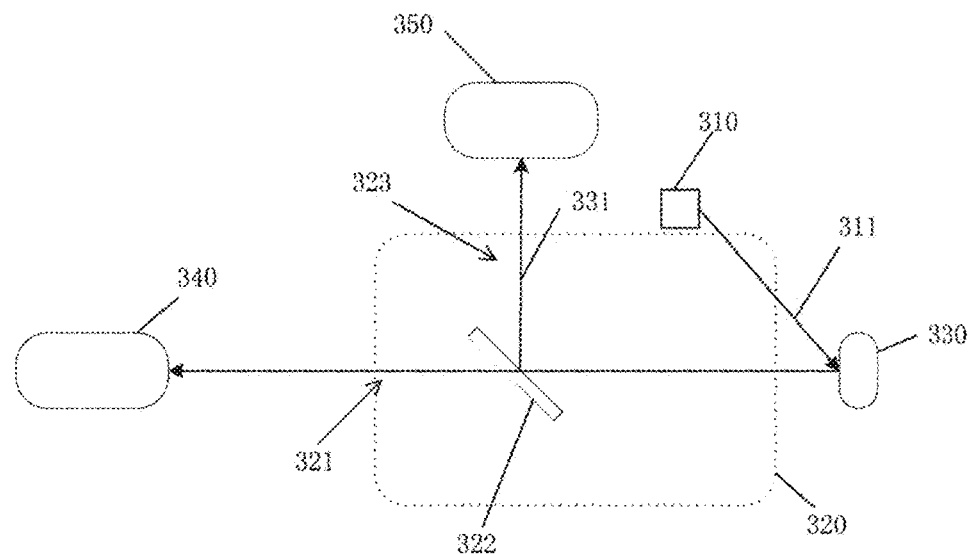
FIG. 5 is a schematic view showing a Raman spectrum-based object inspection apparatus according to an embodiment of the disclosed technology.

FIG. 5 is a schematic view showing a structure of the Raman spectrum-based object inspection apparatus 300a according to an embodiment of the disclosed technology. The Raman spectrum-based object inspection apparatus 300 includes a laser device 310 configured to emit an excited light 311; an optical device 320 configured to guide the excited light 311 to the object 330 to be detected and collect a light signal from the object 330; a spectrometer 340 configured to split the collected light signal to generate Raman spectrum of the object 330; and a security detector 350 configured to detect an infrared light 331 emitted from the object 330. As an example, the Raman spectrum of the object 330 generated by the spectrometer 340 may be compared with the Raman spectra of the known substances to determine the composition of the object 330. The comparing may be implemented for example by the computer or the processor.

During the Raman detection, security accident may occur typically due to temperature rise caused by heat absorption of sample and thereby ablation, even ignition and explosion phenomenon of the object. In the embodiment of the disclosed technology, the security detector 350 (for example, an infrared detector) is used to detect the infrared light 331 emitted by the object 330, so as to monitor the temperature of the object 330. It is because the radiation energy of the infrared light typically increases as the temperature of the object rises. The variation of temperature of the object 330 can be found by monitoring the radiation energy of the infrared light, so as to avoid security accident.

Figure 6:
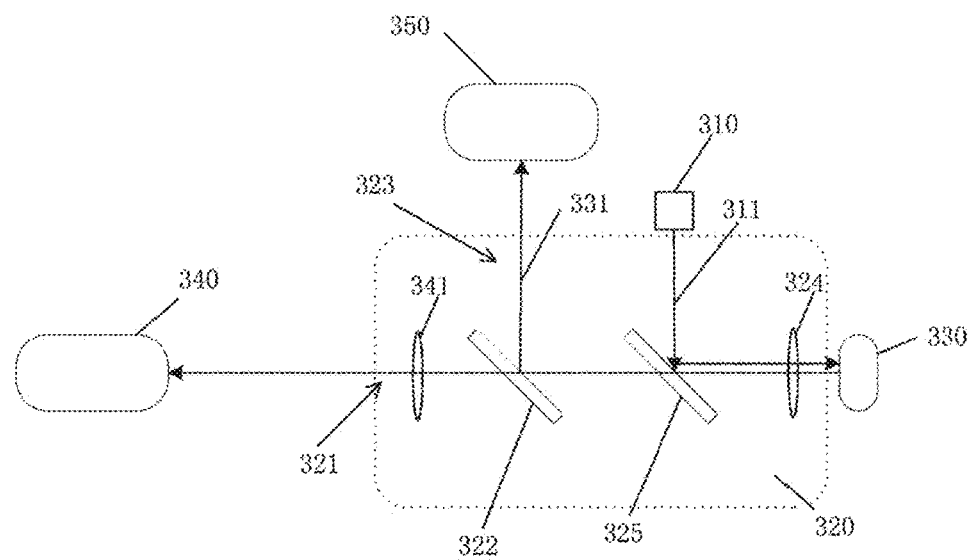
FIG. 6 is a schematic view showing a Raman spectrum-based object inspection apparatus according to another embodiment of the disclosed technology.

In an example, as shown in FIG. 6, the optical device 320 may include a Raman scattering light signal collection optical path 321 configured to collect the Raman scattering light signal from the object 330. A first beam splitter 322 is provided in the Raman scattering light signal collection optical path 321. The first beam splitter 322 is arranged to form an infrared radiation branch 323 from the Raman scattering light signal collection optical path 321, to guide the infrared light from the object 330 towards the security detector 350. The first beam splitter 322 can extract the infrared light emitted from the object 330 from the Raman scattering light signal collection optical path 321, thus it may detect the infrared light while preventing the Raman scattering light signal from being affected to the largest extent. As an example, the first beam splitter 322 may reflect the infrared light in a response waveband of the security detector to the security detector to the largest extent while preventing the Raman scattering light signal (generally in a range of 0-3000 cm$^{-1}$) from being affected as far as possible. Certainly, it may also process the infrared light in the infrared radiation branch 323, such as select waveband of the infrared light, or converge the infrared light, as required.

In the above example, the optical path along which the infrared light travels and the optical path along which the Raman scattering light travels are same at their front ends (at the end close to the object 330). The infrared light collected by this way can better exhibit actual temperature of the object 330.

As an example, the first beam splitter 322 is a short pass dichroic beam splitter arranged to reflect the light having a wavelength greater than a predetermined wavelength towards the security detector 350 while transmitting the light having a wavelength less than the predetermined wavelength through the short pass dichroic beam splitter. For example, the predetermined wavelength may be in a range of 700 nanometers to 300 micrometers, for example, between 900 nanometers and 1500 nanometers, for example, the predetermined wavelength may be arranged as 1200 nanometers. However, the predetermined wavelength of the short pass dichroic beam splitter is not limited to this range in the embodiments of the disclosed technology. Typically, the wavelength range of the Raman spectrum processed by the spectrometer in the Raman spectrum-based object inspection apparatus is from 550 to 900 nanometers. The light having the wavelength less than the predetermined wavelength may be transmitted through the short pass dichroic beam splitter (for example, the transmissivity may be 90% or more), which will substantially have no influence on the Raman spectrum detection. In this way, the light having the wavelength greater than the predetermined wavelength can be reflected into the infrared radiation branch to be transmitted to the security detector 350. Correspondingly, the infrared light will be received and analyzed by the security detector. A typical response waveband of the security detector may for example be 1500 to 3000 nanometers. However, the embodiments of the disclosed technology are not limited to this.

Although the first beam splitter 322 has been explained in the above example with reference to the short pass dichroic beam splitter, it is not intended to limit embodiments of the disclosed technology. Alternatively, the first beam splitter 322 may be implemented by any other wavelength selection beam splitting components known in the art.

In an example, in the exemplified Raman spectrum-based object inspection apparatus 300b shown in FIG. 6, a first converging lens 324, a second converging lens 341 and a second beam splitter 325 may also be provided in the Raman scattering light signal collection optical path 321. The first converging lens 324 is configured to converge the excited light 311 to the object 330 and collect a light signal from the object 330. The second converging lens 341 is configured to converge the collected light signal to the spectrometer. The second beam splitter 325 is arranged between the first converging lens 324 and the first beam splitter 322 in the Raman scattering light signal collection optical path 321 and arranged to reflect the excited light 311 from the laser device 310 towards the first converging lens 324 and transmit at least a part of the reflected light collected by the first converging lens 324 from the object 330 through the second beam splitter 325 to the first beam splitter 322 or the second converging lens 341. In this example, the part of the optical path by which the excited light 311 is guided to the object 330 and the part of the Raman scattering light signal collection optical path 321 between the second beam splitter 325 and the object 330 coincide with each other. In the optical path, the first beam splitter 322 is located downstream of the second beam splitter 325, which may avoid disturbance to the front end of the optical path.

Figure 11:
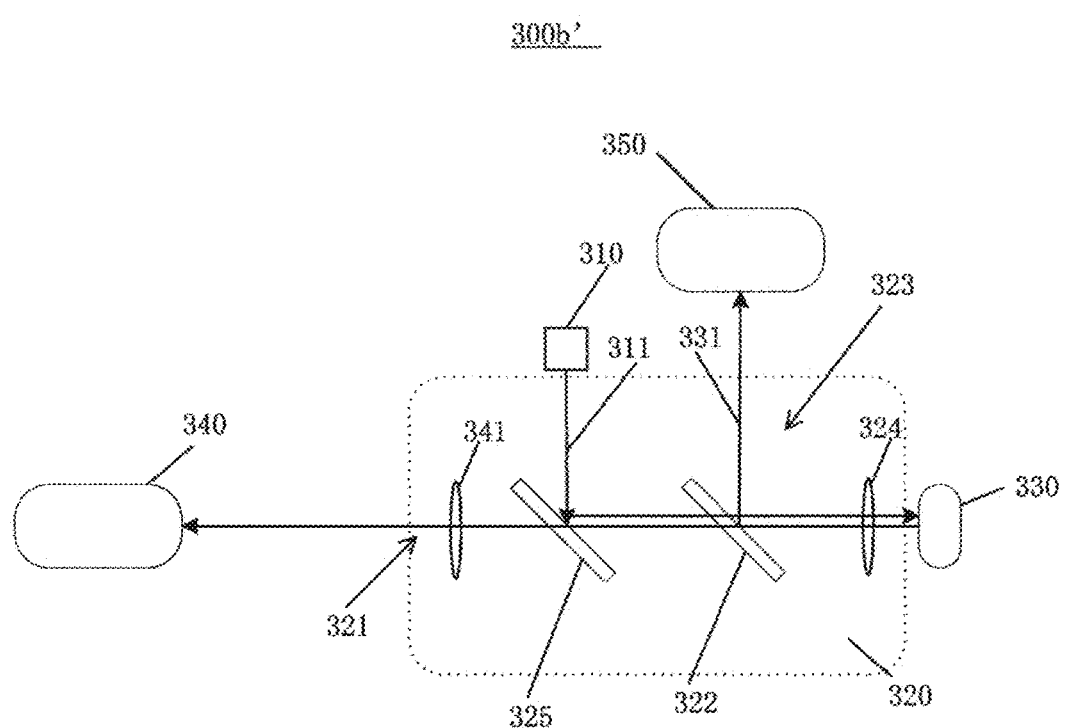
FIG. 11 is a schematic view showing a Raman spectrum-based object inspection apparatus according to a yet still further embodiment of the disclosed technology.

As an example, the positions of the first beam splitter 322 and the second beam splitter 325 in FIG. 6 may be exchanged. For example, as shown in FIG. 11, in the Raman spectrum inspection apparatus 300b', the second beam splitter 325 is located between the first beam splitter 322 and the second converging lens 341 in the Raman scattering light signal collection optical path 321.

As an example, the second beam splitter 325 may be a long pass dichroic beam splitter, that is, it only permits the light having the wavelength greater than a certain threshold to be transmitted through it while blocking the light having the wavelength less than the threshold. It has an advantage of reducing Rayleigh scattering light from the object 330 to be detected. While producing the Raman scattering light, the object 330 often may produce the Rayleigh scattering light which has a wavelength less than that of the Raman scattering light. The threshold of the long pass dichroic beam splitter may be arranged to reduce, even eliminate the Rayleigh scattering light having shorter wavelength, to enhance the signal noise ratio of the signal of the Raman scattering light. The specific threshold of the long pass dichroic beam splitter may be selected as required in practical measurement. In the embodiment of the disclosed technology, the second beam splitter 325 is not limited to the long pass dichroic beam splitter, for example, the second beam splitter 325 may be implemented by any other beam splitting components known in the art.

In an example, in order to better suppress the Rayleigh scattering light, a long pass optical filter or a notch optical filter 326 may also be arranged downstream of the first beam splitter in the Raman scattering light signal collection optical path 321 and configured to filter out the Rayleigh scattering light in the light signal passing through the first beam splitter. Certainly, the embodiments of the disclosed technology are not limited to this, for example, no long pass optical filters or notch optical filters may be provided.

Figure 7:
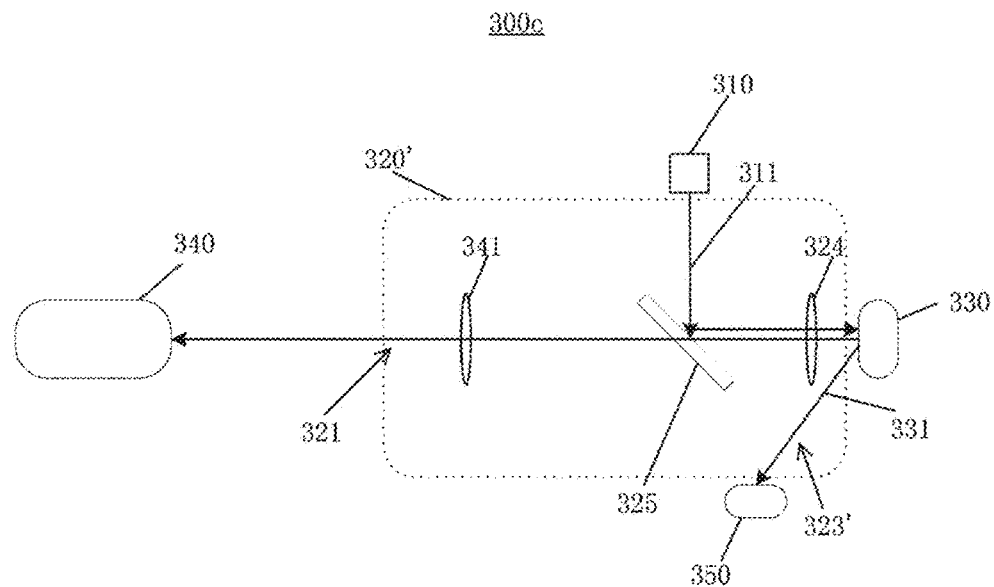
FIG. 7 is a schematic view showing a Raman spectrum-based object inspection apparatus according to a further embodiment of the disclosed technology.
Figure 8:
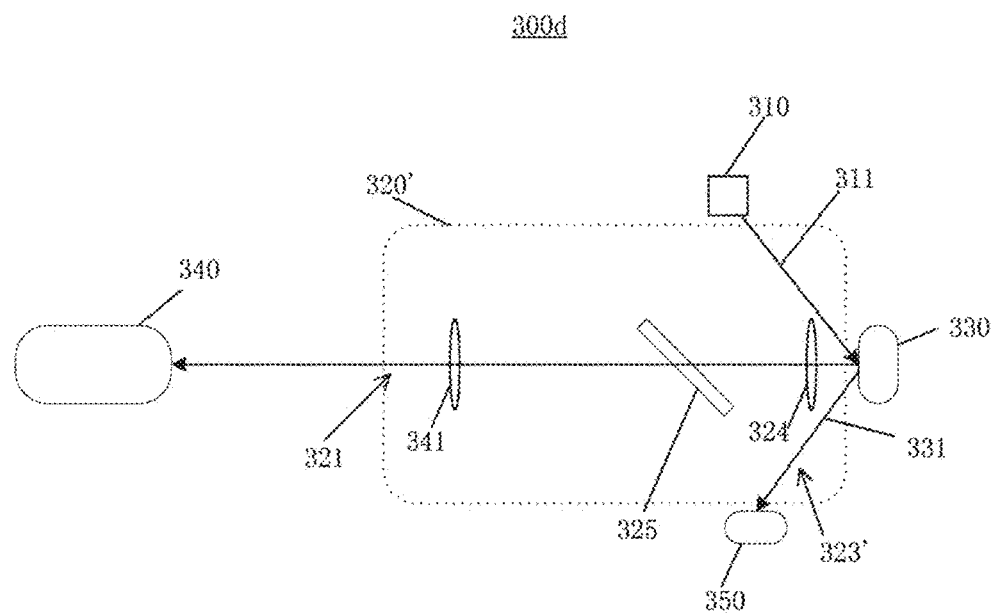
FIG. 8 is a schematic view showing a Raman spectrum-based object inspection apparatus according to a yet further embodiment of the disclosed technology.

In another example, as shown in FIG. 7 and FIG. 8, the optical device 320' may further include: a Raman scattering light signal collection optical path 321 configured to collect the Raman scattering light signal from the object; and an infrared light collection optical path 323' configured to collect the infrared light from the object 330. Other than the infrared radiation branch 323 in the example shown in FIG. 5 and FIG. 6, the infrared light collection optical path 323' is separated completely from the Raman scattering light signal collection optical path 321. In this way, the original optical path structure of the Raman spectrum inspection apparatus may be remained as far as possible. The security detector 350 may be arranged at any position close to the object 330 as long as the intensity of the infrared signal may satisfy the detection requirements of the security detector 350.

The exemplified Raman spectrum-based object inspection apparatus 300c shown in FIG. 7 is same as the exemplified Raman spectrum-based object inspection apparatus 300d shown in FIG. 8, except the following structure: in FIG. 7, the part of the optical path by which the excited light 311 is guided to the object 330 and the part of the Raman scattering light signal collection optical path 321 between the second beam splitter 325 and the object 330 coincide with each other while in FIG. 8, the optical path by which the excited light 311 is guided to the object 330 is separated completely from the Raman scattering light signal collection optical path 321 (or called as "the excited light 311 is irradiated off-axis to the object 330 to be detected").

In the embodiments shown in FIG. 5 and FIG. 8, as an example, the excited light may be redirected by some optical elements (such as a reflector) before it is irradiated to the object 330, such that the excited light can be guided conveniently and correctly to the object 330.

Figure 9:
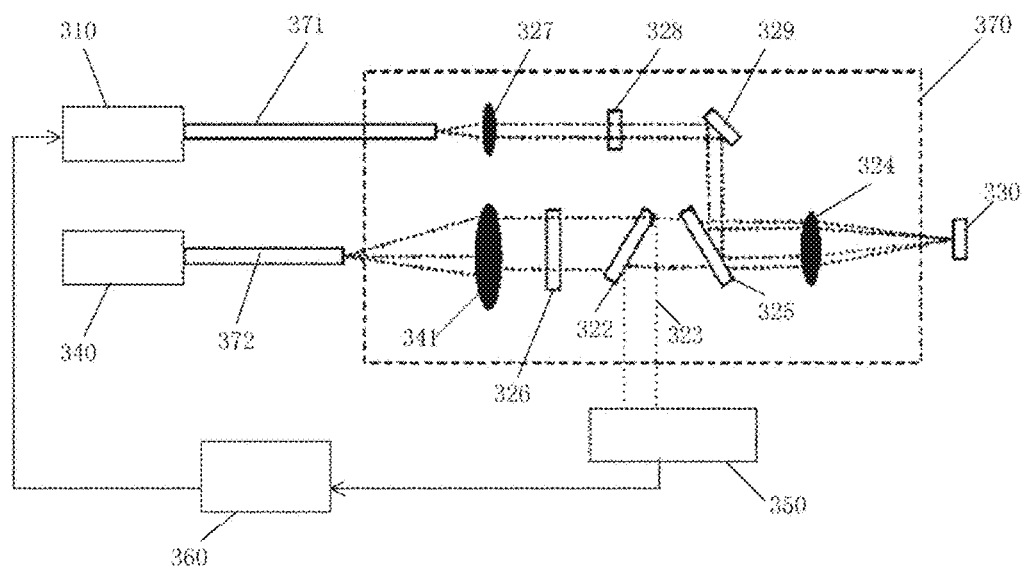
FIG. 9 is a schematic view showing a Raman spectrum-based object inspection apparatus according to a still further embodiment of the disclosed technology.

As shown in FIG. 9, in an example, the Raman spectrum-based object inspection apparatus 300e may further include a controller 360. The controller 360 is configured to receive the detection results of the security detector 350 and send a control signal to the laser device 310. The controller 360 may be configured to reduce power of the laser device 310 or switch off the laser device 310 when the radiation energy of the infrared light detected by the security detector 350 exceeds a predetermined threshold. As an example, there is a correspondence relation between the temperature of the object 330 and the radiation energy of the infrared light emitted by the object 330, thus the predetermined threshold of the radiation energy of the infrared light set in the controller 360 may correspond to a temperature value not greater than the maximum permissible temperature of the object 330, so as to prevent the object 330 from being destroyed due to high temperature. The controller 360 may be implemented by components such as an integrated circuit, a signal processor, a computer or the like.

As an example, the optical device 320 may be integrated in an optical fiber probe 370. The excited light 311 emitted by the laser device 310 may be guided into the optical fiber probe 370 by a guiding optical fiber 371. The optical fiber probe 370 transmits the collected Raman scattering light signal by a collection optical fiber 372 to the spectrometer 340. Certainly, the optical device 320 may also be constructed by separate optical elements. However, the optical fiber probe 370 may improve stability of the system.

As an example, the excited light may also pass through a collimating lens 327 and a narrow band optical filter 328 before arriving at the second beam splitter 325 or the first converging lens 324. The collimating lens 327 may convert the excited light into a substantially parallel light beam to improve directivity and optical efficiency. The narrow band optical filter 328 may remove disturbance to enhance the signal to noise ratio of the excited light in a desired waveband. As an example, in order to fold the optical path, one or more deflecting mirrors 329 may also be arranged. As an example, in order that the Raman scattering light signal can better be coupled into the spectrometer 340, the second converging lens 341 may further be arranged upstream of the collection optical fiber 372.

Figure 10:
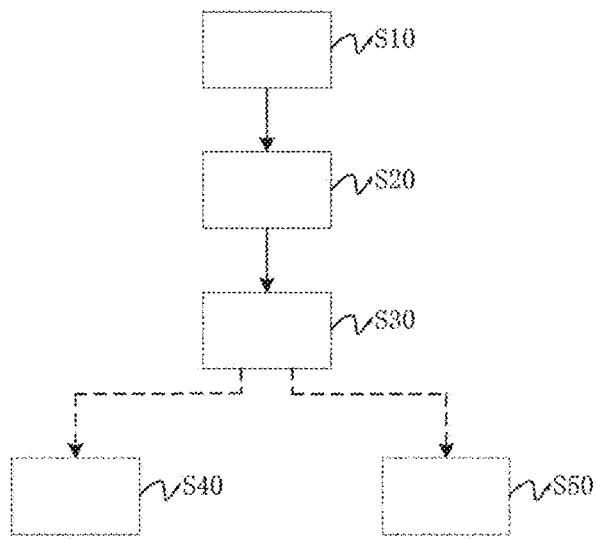
FIG. 10 is a flow chart of a monitoring method of the Raman spectrum-based object inspection apparatus according to an embodiment of the disclosed technology.

An embodiment of the disclosed technology also provides a security monitoring method 200 using a Raman spectrum-based object inspection apparatus. As shown in FIG. 10, the security monitoring method 200 may include:

Step S10: emitting an excited light by a laser device;

Step S20: guiding the excited light to an object to be detected and collecting a Raman scattering light signal from the object; and Step S30: detecting radiation energy of an infrared light emitted from the object to monitor temperature of the object.

The method may be used to monitor the temperature of the object to be detected when the Raman spectrum-based object inspection apparatus works.

As an example, the security monitoring method 200 may further include:

Step S40: reducing power of the laser device or switching off the laser device when the temperature of the object is greater than a predetermined threshold.

The step S40 may be used to monitor whether the temperature of the object is greater than the predetermined threshold (the predetermined threshold may for example 80 Celsius degrees, 100 Celsius degrees, 150 Celsius degrees, or the like, and may be determined depending on the object 330) in real-time when the Raman spectrum-based object inspection apparatus works, so as to ensure security of the detection work.

As an example, the monitoring method 200 may further include:

Step S50: switching off the laser device after the laser device emits the excited light for a predetermined period, and determining security of the object on a basis of variation of temperature of the object in the predetermined period.

The step S50 may be used to estimate security of the detection before the Raman spectrum detection operation is regularly carried out. The predetermined period may for example be 0.5 second, 1 second, 3 second, or the like. If it expects the temperature of the object may be too high, Raman detection parameters (for example laser power, position of the object to be detected, or the like) may be controlled deliberately, so as to avoid security risk in regular detection.

In embodiments of the disclosed technology, any one of the step S40 and step S50 may be used separately, or they may be used in combination. The dashed parts in FIG. 10 represent optional steps.

The above description has explained various embodiments of the above Raman spectrum-based object inspection apparatus and monitoring method thereof by schematic views, flow charts and/or examples. In case that the schematic views, flow charts and/or examples each include one or more functions and/or operations, the skilled person in the art should understand that each function and/or operation in such schematic views, flow charts and/or examples may be implemented separately and/or collectively by various structures, hardware, software, firmware or any combination of them in essential. In an embodiment, some parts of the subject of the embodiment of the disclosed technology may be implemented by Application Specific Integrated Circuits (ASIC), Field Programmable Gate Arrays (FPGA), Digital Signal Processors (DSP) or other integrated forms. However, the skilled person in the art should understand that some aspects of the embodiments disclosed herein may be implemented equally in the integrated circuit entirely or partly, implemented as one or more computer programs running on one or more computers (for example, implemented as one or more programs running on one or more computer systems), implemented as one or more programs running on one or more processors (for example, implemented as one or more programs running on one or more microprocessors), implemented as firmware, or implemented as any combination of the above methods in essential. From the disclosed technology, the skilled person in the art has capability of designing circuits and/or writing software and/or firmware codes. Furthermore, the skilled person in the art will appreciate that the mechanism of the subject of the disclosed technology may be delivered as various forms of program products, and the exemplified embodiments of the subject of the disclosed technology may be applicable independent of the specific types of the signal carrying media that perform the delivery in practice. Examples of the signal carrying media include, but not limited to: recordable media, such as a floppy disc, a hard disk drive, an optical disc (CD, DVD), a digital magnetic tape, a computer memory or the like; and transmission media such as digital and/or analogue communication media (for example, an optical fiber cable, a wave guide, a wired communication link, a wireless communication link or the like).

All of the above embodiments of the disclosed technology may be combined freely to form other embodiments unless there are technical barriers or contradictions. These other embodiments will also fall within scope of the disclosed technology.

Although the disclosed technology has been explained with reference to the drawings, the embodiments shown in the drawings are only illustrative, instead of limiting the disclosed technology. Scales in the drawings are only illustrative, instead of limiting the disclosed technology.

Although some embodiments of the general inventive concept are illustrated and explained, it would be appreciated by those skilled in the art that modifications and variations may be made in these embodiments without departing from the principles and spirit of the general inventive concept of the disclosed technology, the scope of which is defined in the appended claims and their equivalents. The various features and processes described herein may be implemented independently of one another, or may be combined in various ways. All possible combinations and sub combinations are intended to fall within the scope of this disclosure. In addition, certain methods or process blocks may be omitted in some implementations. The methods and processes disclosed herein are also not limited to any particular sequence, and the blocks or states relating thereto can be performed in any other sequences that are appropriate. For example, described blocks or states may be performed in an order other than that specifically disclosed, or multiple blocks or states may be combined in a single block or state. The example blocks or states may be performed in serial, in parallel, or in some other manner as appropriate. Blocks or states may be added to or removed from the disclosed example embodiments as suitable. The example systems and components described herein may be configured differently than described. For example, elements may be added to, removed from, or rearranged compared to the disclosed example embodiments.

While certain embodiments have been described, these embodiments have been presented by way of example only, and are not intended to limit the scope of the disclosure. Indeed, the novel devices, systems, apparatus, methods, and systems described herein may be embodied in a variety of other forms; furthermore, various omissions, substitutions and changes in the form of the methods and systems described herein may be made without departing from the spirit of the disclosure. For example, while blocks are presented in a given arrangement, alternative embodiments may perform similar functionalities with different components and/or circuit topologies, and some blocks may be deleted, moved, added, subdivided, combined, and/or modified. Each of these blocks may be implemented in a variety of different ways. Any suitable combination of the elements and acts of the various embodiments described above can be combined to provide further embodiments.

What is claimed is:

1. A Raman spectrum-based object inspection apparatus, comprising:
    a laser device configured to emit a laser;
    an optical guiding device configured to guide the laser to an object to be detected and collect a Raman scattering light from the object;
    a spectrum generator configured to receive the Raman scattering light collected by the optical guiding device and generate a Raman spectroscopic signal;
    a spectrum analyzer configured to analyze the Raman spectroscopic signal to obtain an inspection result; and
    a monitoring device configured to monitor a state of the object and control an object inspection operation depending on the state of the object,
    wherein the monitoring device comprises:
    an information acquiring unit configured to acquire information on the state of the object; and
    a control unit configured to start or terminate the object inspection operation depending on the information on the state of the object, and
    wherein the information acquiring unit comprises a photographic unit configured to shot a detected location of the object to acquire information on color of the detected location as the information on the state of the object.

2. The Raman spectrum-based object inspection apparatus of claim 1, wherein the control unit is configured to terminate the object inspection operation when the color of the detected location is a predetermined color.

3. The Raman spectrum-based object inspection apparatus of claim 1, wherein the information acquiring unit comprises a temperature measuring unit configured to measure a temperature of the object in the object inspection operation.

4. The Raman spectrum-based object inspection apparatus of claim 3, wherein the control unit is configured to terminate the object inspection operation when a slope of variation of the temperature or amplitude of the temperature of the object exceeds a predetermined threshold.

5. The Raman spectrum-based object inspection apparatus of claim 3, wherein the temperature measuring unit comprises an infrared temperature measuring device.

6. The Raman spectrum-based object inspection apparatus of claim 1, wherein the information acquiring unit further comprises a laser irradiation danger recognizing unit configured to recognize whether a non-irradiated target falls within a region which is being irradiated by the laser or will be irradiated by the laser.

7. The Raman spectrum-based object inspection apparatus of claim 6, wherein the non-irradiated target comprises a face of a person.

8. The Raman spectrum-based object inspection apparatus of claim 1, wherein the monitoring device further comprises a recording unit configured to record a physical image of the object.

9. The Raman spectrum-based object inspection apparatus of claim 1, wherein the object inspection operation comprises emitting the laser by the laser device.

10. The Raman spectrum-based object inspection apparatus of claim 1, further comprising a weight recognizing device configured to identify the object depending on weight of the object.

11. The Raman spectrum-based object inspection apparatus of claim 10, wherein the weight recognizing device comprises:
 a weighing unit configured to measure the weight of the object;
 a storing unit configured to store predetermined reference weights and a database of corresponding barcodes;
 a comparing unit configured to compare the measured weight of the object with the reference weights to determine the barcode corresponding to the reference weight which is closest to the weight of the object; and
 an outputting unit configured to output the determined barcode as a weight recognizing result.

12. A Raman spectrum-based object inspection method, comprising:
 monitoring a state of an object to be detected to determine whether the state of the object is normal or abnormal;
 when the state of the object is normal, starting a laser device to emit a laser to the object and collecting a Raman scattering light from the object to detect a Raman spectrum of the object; otherwise, when the state of the object is abnormal, terminating the laser device to stop emitting the laser to interrupt detection,
 wherein the state of the object comprises a color of the object and the abnormal state of the object comprises a predetermined color of the object while the normal state of the object comprises any colors of the object other than the predetermined color.

13. The Raman spectrum-based object inspection method of claim 12, further comprising: when the state of the object is normal, starting a real-time monitoring of the temperature of the object during detection, and when the temperature of the object is found to exceed a predetermined threshold, terminating the laser device to stop emitting the laser to interrupt the detection.

14. The Raman spectrum-based object inspection method of claim 12, further comprising: comparing the detected Raman spectrum with reference Raman spectra and outputting results of the comparing.

* * * * *